United States Patent [19]

Suekane

[11] Patent Number: 5,618,366
[45] Date of Patent: Apr. 8, 1997

[54] WELDING METHOD FOR DISPOSABLE DIAPERS

[75] Inventor: Makoto Suekane, Kawanoe, Japan

[73] Assignee: Uni-Charm Corporation, Ehime-ken, Japan

[21] Appl. No.: 414,570

[22] Filed: Mar. 31, 1995

Related U.S. Application Data

[62] Division of Ser. No. 242,975, May 16, 1994.

[30] Foreign Application Priority Data

May 19, 1993 [JP] Japan ................. 5-117345

[51] Int. Cl.$^6$ .............. A61F 13/15; A41B 9/12; B32B 31/10; B32B 31/20
[52] U.S. Cl. ........... 156/73.1; 156/204; 156/217; 156/227; 156/292; 156/308.4; 156/324.4; 604/385.1; 604/396
[58] Field of Search ................. 156/73.1, 73.4, 156/73.5, 163, 164, 308.4, 324.4, 204, 217, 227, 292; 604/358, 365–367, 370, 372, 385.1, 393, 396

[56] References Cited

U.S. PATENT DOCUMENTS 4,205,679  6/1980  Repke et al. ............... 604/366
4,743,241  5/1988  Igaue et al. .
5,507,895  4/1996  Suekane ................. 156/73.1

FOREIGN PATENT DOCUMENTS

| 0234658 | 9/1987 | European Pat. Off. . |
| 0241925 | 10/1987 | European Pat. Off. . |
| 0531666 | 3/1993 | European Pat. Off. . |
| 5-15551 | 1/1993 | Japan . |
| 2170394 | 8/1986 | United Kingdom . |
| 2257652 | 1/1993 | United Kingdom . |

*Primary Examiner*—Adrienne C. Johnstone
*Attorney, Agent, or Firm*—Lowe, Price, LeBlanc & Becker

[57] ABSTRACT

A welding method for a disposable diaper includes the steps of putting wing-like portions 21, 22 provided on front and rear bodies 5, 6 including a topsheet 2, a backsheet 3 and a core 4 sandwiched therebetween, one upon another, with the topsheet disposed face to face; placing covering sheets 20 on an outer surface of the wing-like portions, both the covering sheets and the wing-like portions having a melting point higher than the melting point of the backsheet; and welding, under heat and pressure exerted from above the covering sheets, laterally opposite side edges of the wing-like portions.

8 Claims, 3 Drawing Sheets

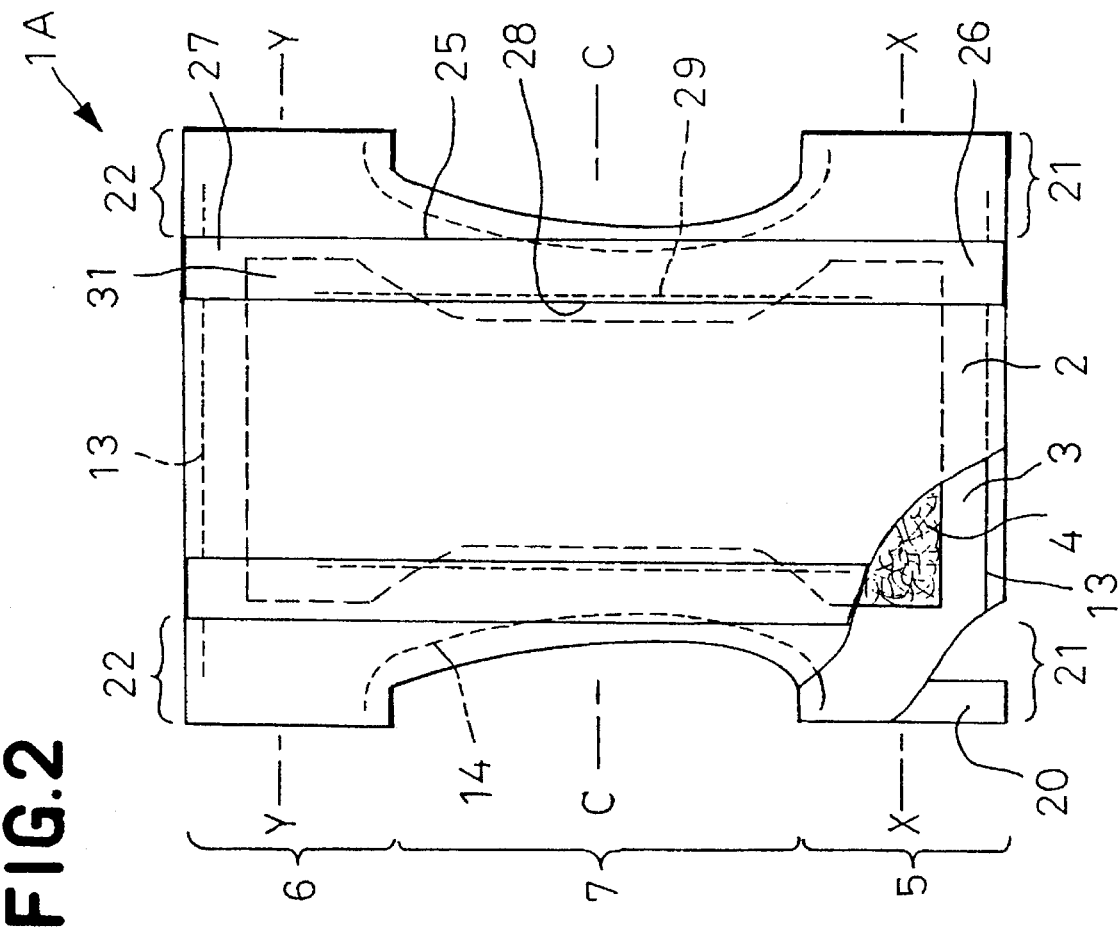
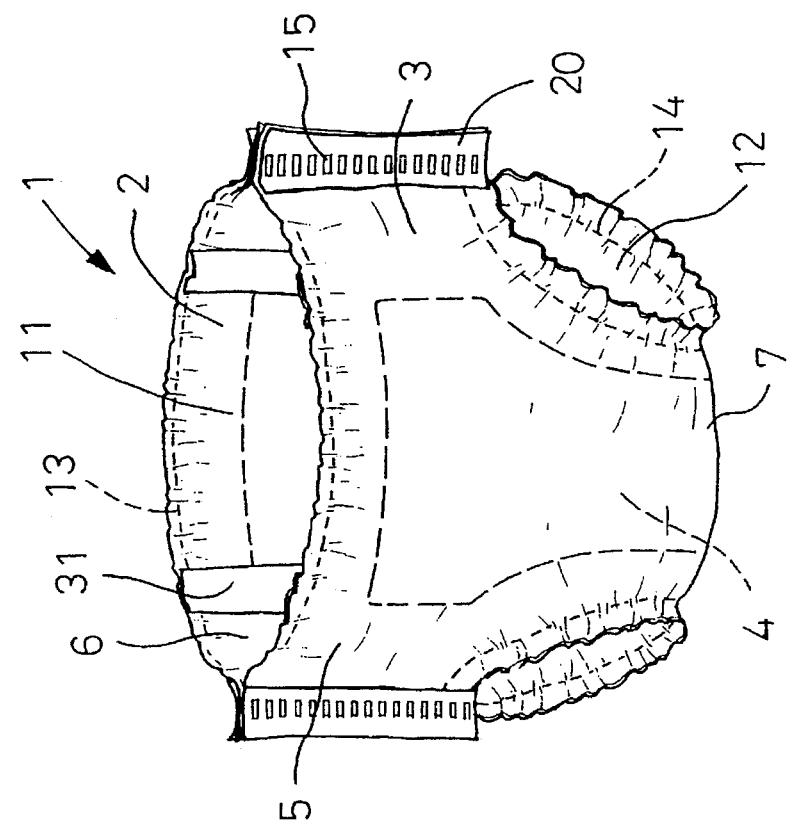

WELDING METHOD FOR DISPOSABLE DIAPERS

This application is a division of application Ser. No. 08/242,975 filed May 16, 1994.

BACKGROUND OF THE INVENTION

The present invention relates to a method of welding a disposable diaper along laterally opposite side edges at its waist level.

One example of a pant-type of disposable diapers is disclosed in Japanese patent application Disclosure No. 5-15551. In that reference, a diaper comprises top- and backsheets and a liquid-absorbent core sandwiched therebetween. The diaper is folded along a transverse center line passing through a crotch zone so that front and rear bodies are positioned one upon another. The top- and backsheets are ultrasonically welded together along laterally opposite side edges at its waist level to obtain a pant-type of a configuration. The top- and backsheets may be formed, for example, by nonwoven fabric of thermoplastic synthetic resin which can be ultrasonically heated.

Nonwoven fabric employed in the technique disclosed in said Disclosure as material for the top- and backsheets may be made from fibers of the same type as mentioned above and heated until the nonwoven fabric exhibits an appropriate viscosity so that a weld zone of the top- and backsheets presents a smoothly finished appearance. However, if the topsheet formed of nonwoven fabric of polypropylene fiber having a relatively high melting point is combined with the backsheet formed of polyethylene sheet or film having a relatively low melting point, the polyethylene sheet will melt earlier than the polypropylene fiber when the diaper is folded and subjected to the ultrasonic treatment. In consequence, the polyethylene sheet may melt to an excessively low viscosity and stick to a horn pressed against this sheet during the ultrasonic treatment. The polyethylene sheet which has stuck to the horn will, once cooled, result in a rough, itchy and uncomfortable surface and spoil the aesthetical appearance of the diaper. If the polyethylene sheet remains stuck to the horn, no accurate clearance can be assured between the horn and an anvil during the next cycle of the ultrasonic treatment, thus making the continuous treatment difficult.

Accordingly, it is a principal object of the invention to solve the aforementioned problem by placing a covering sheet having a melting point higher than a melting point of a backsheet upon an outer surface of the backsheet and bringing it in contact with the pressing means such as a horn for an ultrasonic treatment.

SUMMARY OF THE INVENTION

The object set forth above is achieved, according to the invention, by a welding method for a disposable diaper generally comprising the steps of assembling a liquid-permeable topsheet, a liquid-impermeable backsheet and a liquid-absorbent core sandwiched between these sheets into a configuration of disposable diaper, putting wing-like portions of front and rear bodies outwardly extending from laterally opposite side edges of the core one upon another and welding the wing-like portions under heat and pressure together to form opposite side portions at waist levels of the front and rear bodies. The welding method comprises the steps of assembling topsheet members associated with the topsheet so as to form extensions thereof with the backsheet made of material having a melting point lower than a melting point of the topsheet members to form the wing-like portions, putting the wing-like portions one upon another with the topsheet members disposed face to face inside the diaper, placing covering sheets having a melting point higher than the melting point of the backsheet on an outer surface of the backsheet, and welding the wing-like portions along laterally opposite side edges thereof together with the covering sheets.

Preferably, the melting point of the covering sheets is higher than the melting point of the topsheet members.

According to the welding method as described above, the heating/pressing means such as an ultrasonic horn or a heating element of desired shape is pressed against the sheet portions to be welded together. The covering sheet having a melting point higher than that of the backsheet is brought in contact with the heating/pressing means so as to prevent the molten backsheet from sticking to the heating/pressing means.

BRIEF DESCRIPTION OF THE DRAWINGS

A welding method of the invention will be described in more detail with reference to the accompanying drawings, in which:

FIG. 1 is a perspective view of a pant type disposable diaper;

FIG. 2 is a plan view of the diaper as unfolded;

PREFERRED EMBODIMENTS OF THE INVENTION

Figure 3:
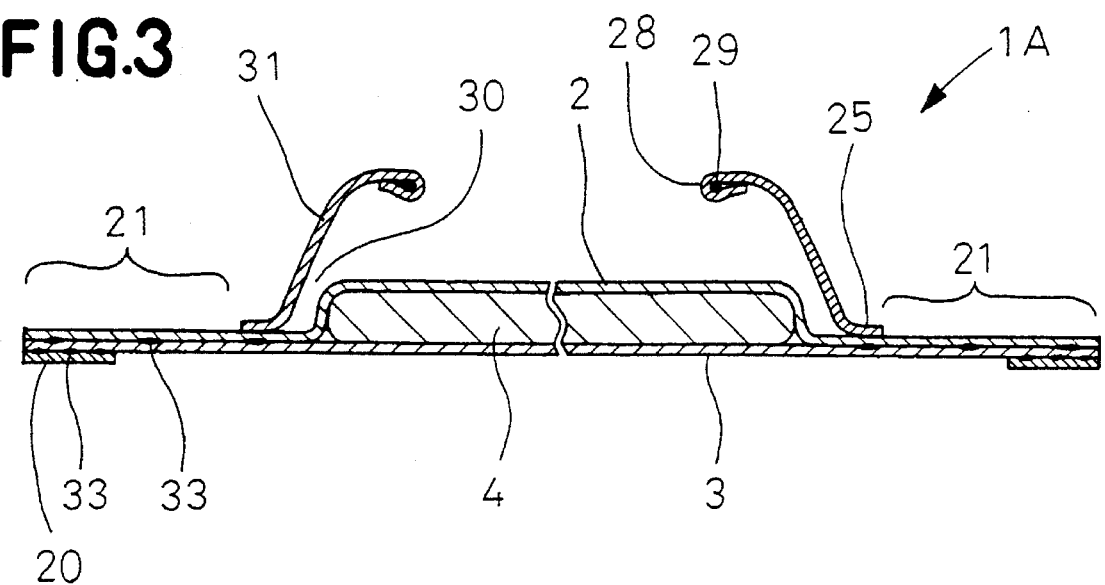
FIG. 3 is a sectional view along a line X—X in FIG. 2.

FIG. 1 is a perspective view showing a pant-type of disposable diaper 1 obtained by a welding method of the invention. The diaper 1 comprises a liquid-permeable topsheet 2 formed of a melt bond nonwoven fabric of polypropylene fiber, a liquid-impermeable backsheet 3 formed of a polyethylene sheet and a liquid-absorbent core 4 sandwiched between these sheets 2, 3. The diaper 1 is also generally configured by a front body 5, a rear body 6 and a crotch zone 7. A waist-opening 11 and respective leg-openings 12 are provided with elastically stretchable members 13, 14, respectively, which are adhesively attached thereto along their peripheries. The front and rear bodies 5, 6 are laid one on top of another with the topsheet 2 disposed face to face inside the diaper 1 and the backsheet 3 is provided along laterally opposite sides of waist portions of the front and rear bodies 5, 6 with covering sheets 20 so that these sheets 2, 3, 20 are welded together by an ultrasonic intermittent weld line (see reference numeral 15) vertically extending along lateral sides of the waist portions.

FIG. 2 is a plan view of the diaper 1A prior to the welding depicted unfolded longitudinally and partially broken away. In the diaper 1A, the waist portions of the front and rear bodies 5, 6 extend outwardly from lateral side edges of the liquid-absorbent core 4 to define wing-like portions 21, 22, respectively. It should be understood that these wing-like portions 21, 22 may be defined by topsheet members and/or backsheet members of the desired characteristics bonded to the topsheet and/or the backsheet to form extensions thereof rather than the top- and backsheets. The wing-like portions 21, 22 carry on their side of the backsheet 3 the previously mentioned polypropylene covering sheets 20. On laterally opposite sides of the diaper 1A inside the wing-like portions 21, 22, there are provided a pair of flaps 31 longitudinally extending on the topsheet 2. Each flap 31 is bonded to the topsheet 2 along its outer edge 25 and its longitudinally opposite ends 26, 27 so that its inner edge 28 may rise from the topsheet 2 under the effect of an elastic member 29 bonded, in a stretched condition, to the inner edge 28.

FIG. 3 is a sectional view along a line X—X in FIG. 2. It should be understood here that a sectional view along a line Y—Y in FIG. 2 is substantially the same as FIG. 3. Over each wing-like portion 21 of the diaper 1A, the top- and backsheets 2, 3 are intermittently bonded to each other by means of hot melt adhesive 33, and the backsheet 3 and the covering sheet 20 are also bonded to each other by means of hot melt adhesive 33. Each flap 31 cooperates with the topsheet 2 to form a pocket 30 opening inwardly of the diaper 1A. The liquid-absorbent core 4 may be bonded, if necessary, to the topsheet 2 and/or the backsheet 3.

Figure 4:
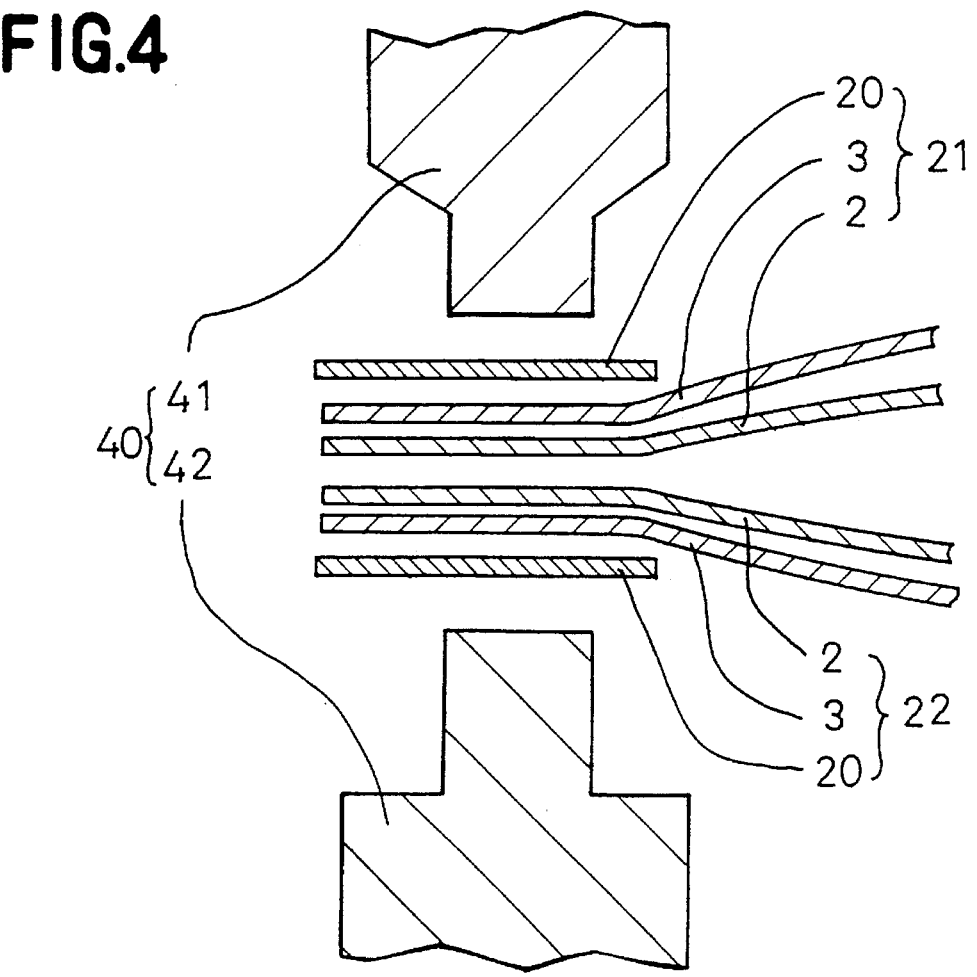
FIG. 4 is a schematic diagram illustrating ultrasonic treatment.

FIG. 4 is a schematic side view illustrating a manner in which said diaper 1A is folded inwardly along a center line C—C in FIG. 2 and the wing-like portions 21, 22 of the front and rear bodies overlapped together are welded together utilizing an ultrasonic welder 40. The welder 40 may be of the conventional type and comprises a horn 41 connected to an ultrasonic oscillator (not shown) and a stationary anvil 42, between which the wing-like portions 21, 22 are held and welded together so as to form a weld zone 15 (FIG. 1) conformable to the shape of the horn 41 at its forward end.

In the ultrasonic treatment of the diaper 1A, the optimal condition of the treatment must be selected to weld together sections of the topsheet 2 folded against each other. During this treatment, the polyethylene sheet forming the backsheet 3 having a melting point lower than a melting point of the polypropylene sheet forming the topsheet 2 is heated earlier to become sticky and, in order to prevent the polyethylene sheet (backsheet 3) from sticking to the horn 41, the polypropylene covering sheet 20 is interposed between the polyethylene sheet (backsheet 3) and the horn 41.

Figure 5A:
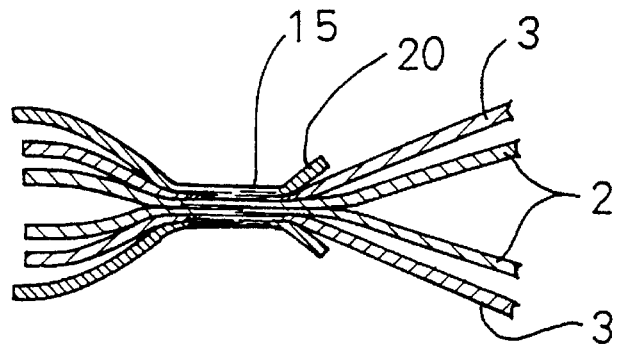
FIGS. 5A and 5B are sectional views of weld zones presenting different configurations.
Figure 5B:
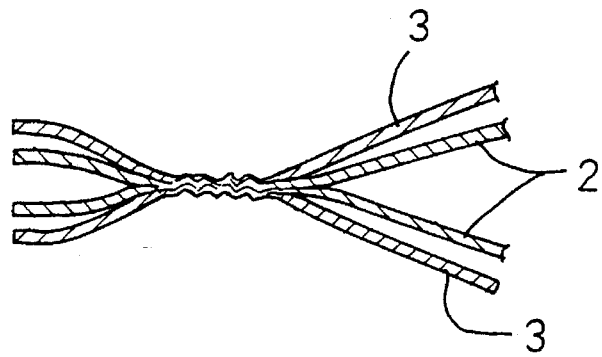

FIGS. 5A and 5B are is a schematic side views of the weld zones obtained by the ultrasonic treatment, wherein FIG. 5A illustrates the weld zone 15 obtained utilizing the covering sheet 20 according to the method of the invention and FIG. 5B illustrates the case in which no covering sheet 20 is utilized. In the case illustrated by FIG. 5A, the decrease of viscosity of the polypropylene sheet (backsheet 3) is not significant and the welding occurs in a rather viscous molten state, so a mark made by the horn 41 on the weld zone 15 is round, resulting in a smooth finish which does not irritate the wearer's skin. In the case illustrated in FIG. 5B, on the other hand, the polyethylene sheet (backsheet 3) is molten and sticks to both the horn 41 and the anvil 42 when the molten state of the polypropylene sheet (topsheet 2) is of a relatively high viscosity, so the weld zone 15a after cooled presents a rough surface giving an itchy stimulus to the wearer's skin.

Figure 6A:
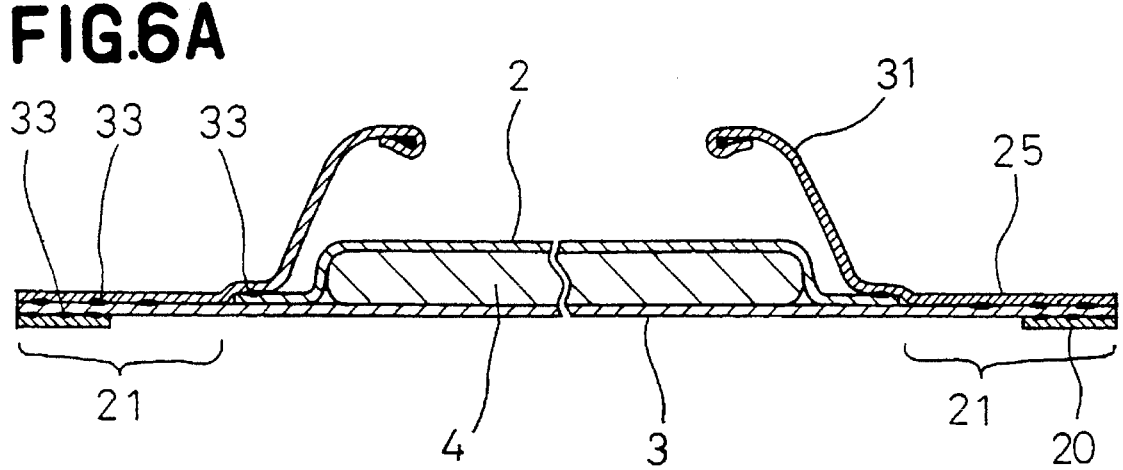
FIGS. 6A and 6B are views similar to FIG. 3 showing different configurations.
Figure 6B:
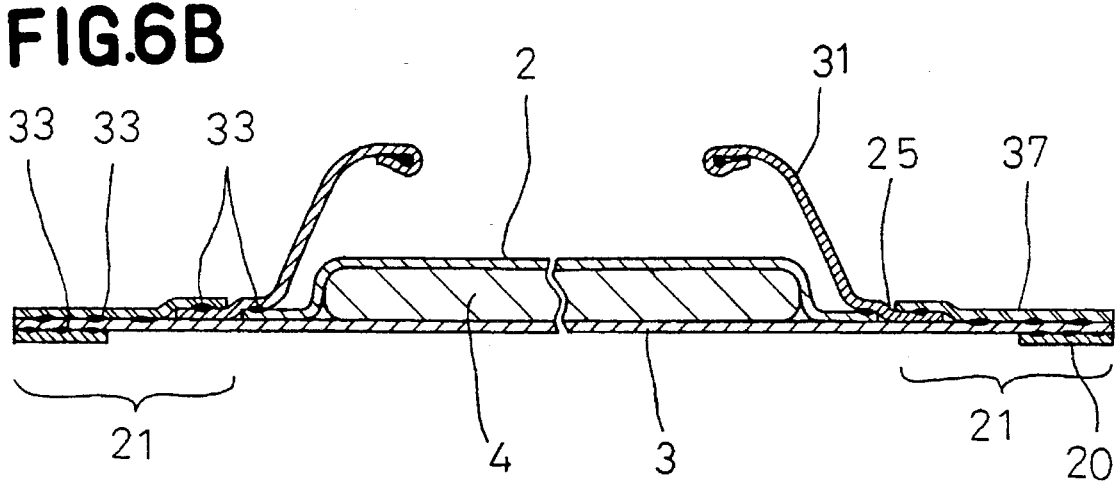

FIGS. 6A and 6B are sectional views showing configurations different from each other and different from the configuration shown by FIG. 3. In FIG. 6A, portions of the topsheet 2 extending from the laterally opposite side edges of the core 4 are extremely small. However, outer zone 25 of each flaps 31 bonded to the topsheet 2 by means of hot melt adhesive 33 is a relatively large and cooperates with the backsheet 3 to from the wing-like portion 21. The front and rear bodies 5, 6 (see FIG. 2) are folded along a boundary line therebetween to put the outer zone 25 on the side of the front body 5 and the outer zone 25 on the side of the rear body 6 together and these outer zones 25 are subjected to the ultrasonic treatment. Each flap 31 is formed by spun bond nonwoven fabric of polypropylene. In FIG. 6B, a topside sheet member of each wing-like portion 21 comprises spun bond nonwoven fabric covering sheet 37 of polypropylene which covers the associated outer zone 25. The topsheet 2, the outer zone 25 and the covering sheet 37 are bonded together by means of hot melt adhesive 33. The front and rear bodies 11, 12 are folded up against to each other so as to place the covering sheet 37 on the side of the front body 11 and the covering sheet 37 on the side of the rear body 12 one on another. This area is then subjected to the ultrasonic treatment. In both configurations shown by (A) and (B), the backsheet 3 is made of polyethylene.

It is also possible without departing from the scope of the invention to form each of the topside sheet member, the backsheet 3 and the covering sheet 20 from a mixture of fibers having different melting points. The differential melting point in each sheet should be understood here as the differential melting point between the composing fibers totally occupying 60% or higher by weight of this sheet.

The melting point of the covering sheet 20 should be higher than the melting point of materials composing the backsheet 3 and, more preferably, equal to or higher than the melting point of the topside sheet member so that the formation of a desirably shallow and small press mark under the heating effect may be facilitated.

When nonwoven fabric composed of polypropylene is used to form the topsheet 2 and the topside sheet member as in the diaper 1 illustrated as an embodiment of the invention, the polypropylene fiber having a relatively high firmness will make the nonwoven fabric cushiony, depending on a fineness as well as a density, and give the wearer a comfortable feel when the diaper 1 is warn. Use of the polyethylene sheet as the backsheet 3 will allow this relatively inexpensive sheet to provide a comfortable soft touch.

It should be understood that the covering sheet 20 may be dimensioned so as to cover a desired area or whole area of the backsheet 3, having been and previously laminated thereon.

According to the welding method of the invention, the covering sheet having a melting point higher than that of the backsheet is interposed between the heating/pressing means such as the ultrasonic horn and the backsheet in order to prevent the molten backsheet from sticking to the heating/pressing means. The present invention avoids the prior art problem resulting, the weld zone after cooling, a rough surface which may give the wearer's skin an itchy stimulus and/or spoil an aesthetic appearance of the diaper. Moreover, according to he present invention, the process of ultrasonic treatment is well stabilized, since no molten sheet material sticks to the horn.

What is claimed is:

1. A welding method for a disposable diaper generally comprising the steps of assembling a liquid-permeable topsheet, a liquid-impermeable backsheet and a liquid-absorbent core sandwiched between these sheets into a configuration of a disposable diaper, putting wing-like portions of front and rear bodies outwardly extending from laterally opposite side edges of said core one upon another and welding said wing-like portions put one upon another under heat and pressure together to form opposite side portions at waist levels of said front and rear bodies, said welding method further comprising the steps of:

assembling topsheet members associated with said topsheet so as to form extensions thereof with said backsheet made of material having a melting point lower than a melting point of said topsheet members to form said wing-like portions, putting said wing-like portions one upon another with said topsheet members disposed face to face inside said diaper, placing covering sheets having a melting point higher than the melting point of said backsheet on an outer surface of said backsheet, and welding said wing-like portions along laterally opposite side edges thereof together with said covering sheets.

2. The method of claim 1, wherein the covering sheets are made of polypropylene.

3. The method of claim 1, wherein the backsheet is made of polyethylene and the covering sheets are made of polypropylene.

4. The method of claim 1, wherein the welding method produces weld zones having a smooth finish.

5. The method of claim 1, wherein the step of putting the wing-like portions one upon another comprises the steps of forming the wing-like portions by bonding supplemental covering sheets to the topsheet, wherein the step of assembling topsheet members associated with said topsheet so as to form extensions thereof with said backsheet comprises assembling said supplemental covering sheets.

6. The method of claim 1, wherein prior to the welding step, the method further comprises the step of bonding a pair of flaps to the topsheet on laterally opposite sides of the absorbent core inside the wing-like portions.

7. The method of claim 6, wherein extensions of the flaps form the wing-like portions of the topsheet.

8. The method of claim 1, wherein prior to the step of putting the wing-like portions one upon another, the method further comprises the step of bonding a pair of flaps to the topsheet on laterally opposite sides of the absorbent core; and wherein the step of putting the wing-like portions one upon another comprises the steps of forming the wing-like portions by bonding supplemental covering sheets to extensions of the flaps outwardly of the flaps, wherein the step of assembling topsheet members associated with said topsheet so as to form extensions thereof with said backsheet comprises assembling said supplemental covering sheets.

* * * * *